United States Patent [19]

Wada et al.

[11] 4,408,847
[45] Oct. 11, 1983

[54] REFRACTORY POWER MEASURING DEVICE

[75] Inventors: Shinji Wada; Yoshinori Oana; Ikuo Kitao; Yasuo Kato; Taketoshi Ishihara, all of Tokyo, Japan

[73] Assignee: Tokyo Kogaku Kikai Kabushiki Kaisha, Japan

[21] Appl. No.: 204,229

[22] Filed: Nov. 5, 1980

[30] Foreign Application Priority Data

Nov. 9, 1979 [JP] Japan .................................. 54-145270

[51] Int. Cl.³ .............................................. A61B 3/10
[52] U.S. Cl. ................................... 351/211; 351/214
[58] Field of Search ................... 351/6, 13, 14, 211, 351/214; 356/124–127

[56] References Cited

U.S. PATENT DOCUMENTS

| | | | |
|---|---|---|---|
| 3,664,631 | 5/1972 | Guyton | 351/6 X |
| 3,669,530 | 6/1972 | Guyton | 351/17 |
| 4,293,199 | 10/1981 | Wada et al. | 351/13 |

FOREIGN PATENT DOCUMENTS 54-69455  6/1979  Japan .
54-102145  8/1979  Japan .

Primary Examiner—F. L. Evans
Attorney, Agent, or Firm—Brumbaugh, Graves, Donohue & Raymond

[57] ABSTRACT

A refractory power measuring device for measuring the refractory power of the human eye or a lens. The device includes a target projecting optical system having two optical elements which are movable along the optical axis of the system independently from each other. The device can measure simultaneously the refractory powers along two astigmatic axes.

5 Claims, 8 Drawing Figures

REFRACTORY POWER MEASURING DEVICE

The present invention relates to a refractory power measuring device for measuring the refractive power of the human eye or a like object.

Known types of refractory power measuring devices include a so-called eye refractometer in which a target image is projected on the fundus of the eye through the eye lens and the refractive power of the eye is measured as the position of the target on the optical axis when the target image is focussed on the retina. In using this eye refractometer, the target for detecting the astigmatic axis projected on the eye is rotated by an optical element such as an image rotator to detect the orientation of the astigmatic axis. The target projected on the eye for measuring the refractive power is then moved in the direction of the optical axis to measure the refractive power along the astigmatic axis. Thereafter, the target for detecting the astigmatic axis is rotated to detect the other astigmatic axis and the orientation of the latter is ascertained in the same manner as above. Moreover, the refractive power along this astigmatic axis is measured in the same manner as described above. Thus, the conventional eye refractometer requires repetition of a troublesome operation. In addition, in the examination of astigmatism which requires two measuring operations for measuring the refractive power, there is a time difference between the first and second measurements. Hence there is a difference in the state of refractive power adjustment of the eye as well as poor eye alignment of the eye, the result being an error in measurement.

Most cases of astigmatism are so-called regular astigmatism in which two astigmatic axes cross each other at a right angle. From this point of view, Japanese Patent Laid-Open Publication No. 69455/1979 proposes a refractive power measurement device in which the detection of the second astigmatic axis between the first and second measurements of the refractive power is omitted. This device can remarkably shorten the time between the first and the second measurements of the refractive power, but requires that the target be moved along the optical axis after the measurement of the refractive power, so that the aforesaid problems attributable to the time difference cannot be eliminated completely.

In an autorefractometer in which judgement regarding focussing of the target image is made wholly mechanically and not by operator observation, measurement is performed in a period of time which is shorter than that required for an involuntary and temporal change in refractive power. Alternatively, the measurement is performed over a sufficiently long time to obtain the mean value of the refractive power by eliminating the involuntary change in the refractive power with time, thereby to diminish the error in measurement.

In this autorefractometer, however, information concerning, for example, cloudiness in the optical system of the eye, fundus abnormality and other states which are beyond the discriminating ability of the device, is included in the information concerning the refractive power, because the judgement or discrimination is performed fully mechanically. This of course leads to an error in measurement. Also, there is a possibility of failing to notice a disease which might have been discovered had use been made of the apparatus which relies upon operator observation and judgement.

Under these circumstances, the present invention seeks to provide a refractive power measuring device capable of simultaneously measuring the refractive powers on two astigmatic axes.

More specifically, the refractive power measuring device of the invention comprises a target composed of two optical elements capable of measuring refractive powers in two orthogonal directions, which optical elements are movable in the direction of respective optical axes independently of each other.

In the operation of the device of the invention, the projected target image is rotated by an image rotator or the like to detect the astigmatic axes. Next, the optical elements of the target are moved simultaneously in the directions of the optical axes to determine the focussing position of the projected image of the refractory power measuring optical element corresponding to one of the astigmatic axes. Thereafter, only the other optical element is moved in the direction of the optical axis to determine the focussing position of the projected image of the other optical element, so that the refractive powers along two astigmatic axes are measured at a time. In addition, since the judgement of the focussed state of the projected image is checked through observation by an operator, cloudiness or any other abnormal eye condition can be discovered.

Such a refractive power measuring device using optical elements as targets which are movable independently of each other for the measurement of refractive powers along two astigmatic axes has been already proposed in U.S. Pat. No. 3,669,530. More specifically, in the refractive power measuring device proposed in this United States Patent, first and second targets are disposed in a tandem manner along the optical axis, and a cylindrical lens is incorporated in order to optically superpose both targets at a reference point. A similar refractive power measuring device is disclosed in Japanese Patent Laid-Open No. 102145/1979. These known refractive power measuring devices have an advantage similar to that of the present invention in that they can measure the refractive powers along two astigmatic axes by two targets movable independently of each other in the direction of the optical axis. However, in these known devices, it is not possible to move one of the targets beyond the other in the direction of the optical axis because two targets are arranged in a tandem manner along the optical axis. Hence, there is a practical limit in the operation of these devices and some inconvenience results when they are used. In addition, it is necessary to provide a cylindrical lens in the optical system in order to make two targets optically coincide with each other.

These problems of the prior art can be solved by the present invention. Namely, in the refractive power measuring device of the invention, two targets are disposed on both sides of the optical axis so that two targets are freely movable in the direction of the optical axis beyond the position of each other on said axis. The device of the invention, therefore, is free from the limitations imposed in the conventional devices and, in addition, does not necessitate the cylindrical lens for optically bringing two targets into coincidence. Preferably, a mechanism for moving two targets simultaneously and a mechanism for moving two targets independently are suitably combined in the refractive power measuring device of the invention.

Hereinafter, the invention will be described in detail through an embodiment applied to a refractometer taking reference to the accompanying drawings, in which.

Figure 1:
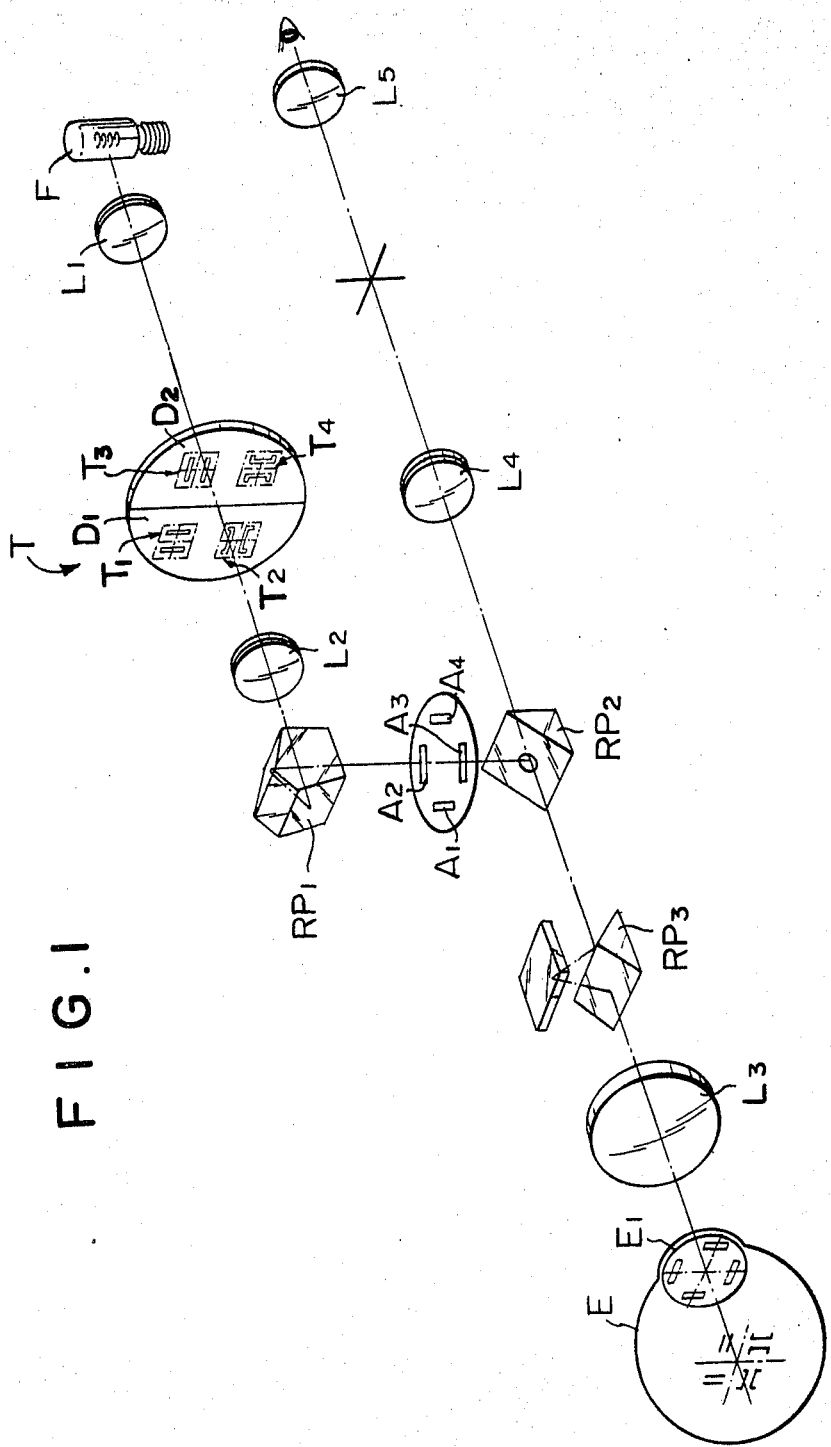
FIG. 1 is a perspective view of the optical system of an eye refractometer in accordance with one embodiment of the present invention.
Figure 1A:
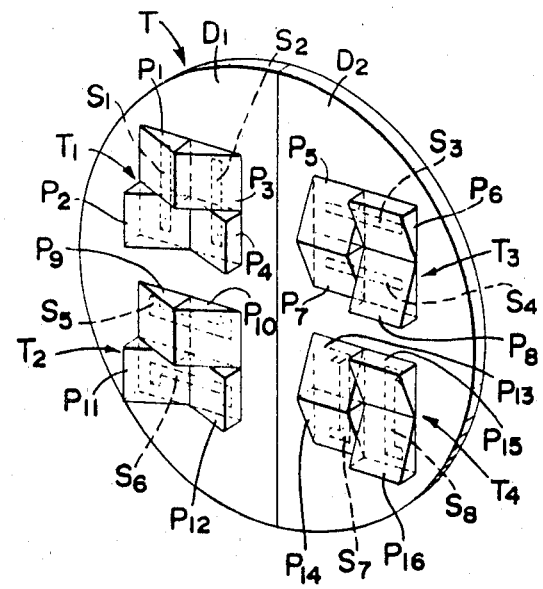
FIG. 1A is an enlarged perspective view of the target.
Figure 2A:
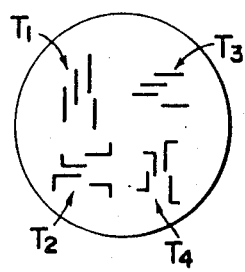
Figure 2B:
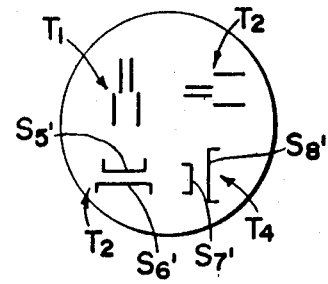
Figure 3:
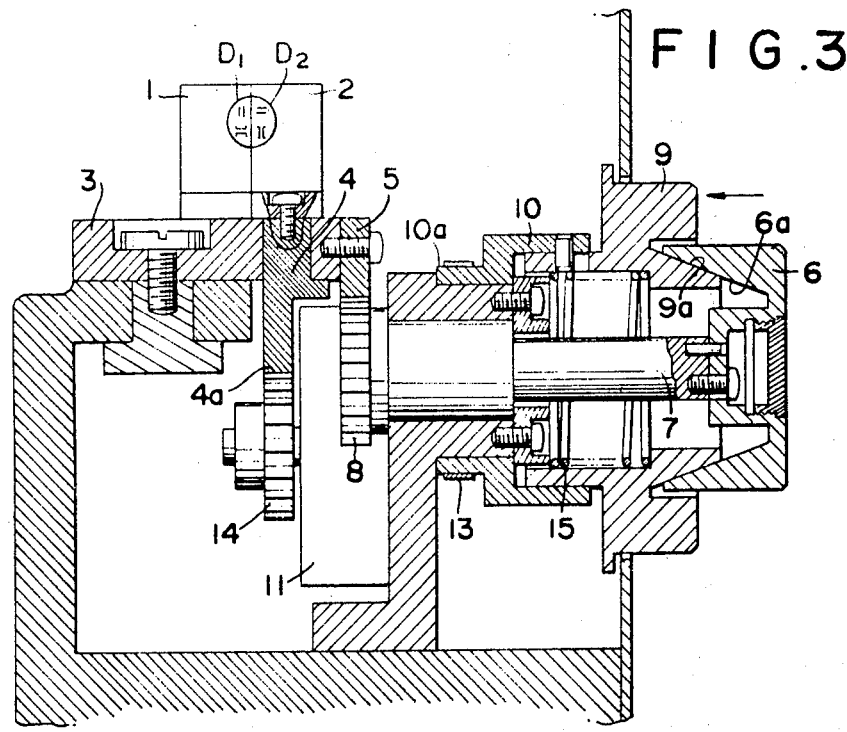
Figure 4:
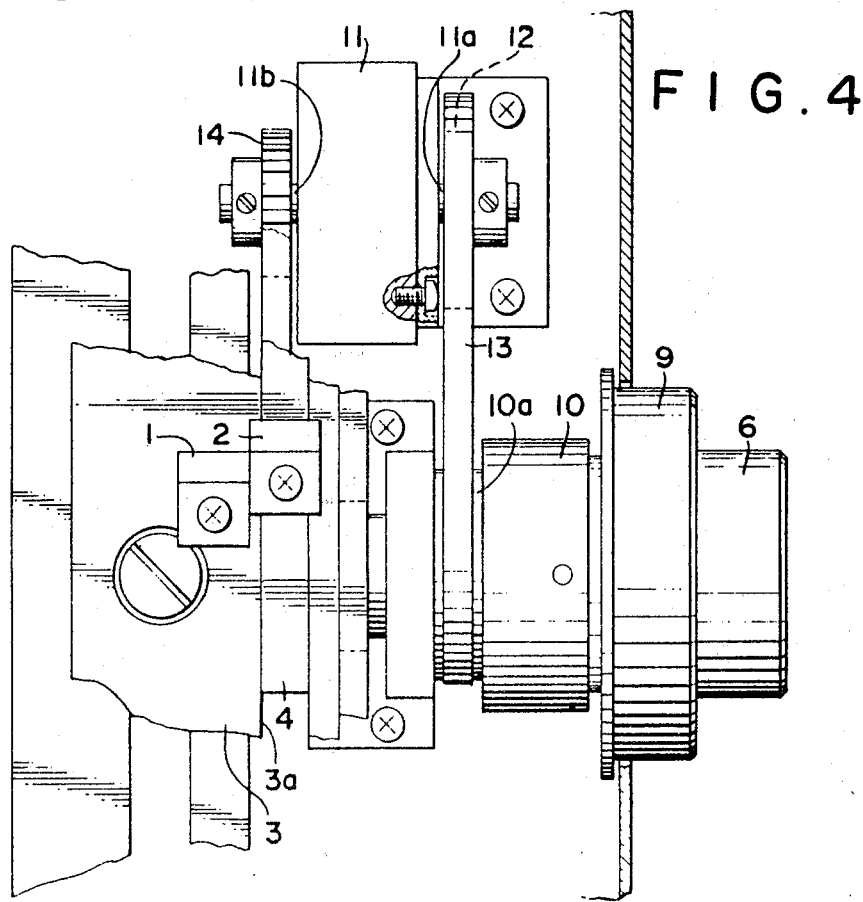

FIGS. 2(a) (b) (c) and (d) show target images; and,

FIGS. 3 and 4 are vertical section and a plan view of one example of the target driving mechanism. Referring to FIGS. 1 and 1A which are schematic perspective view of the optical system of a refractometer in accordance with the invention, the refractometer comprises a projection optical system and an observation optical system. The projection optical system includes a light source F, lenses $L_1$, $L_2$, a pentagonal prism $RP_1$, a prism $RP_2$ with a bore, an image rotator $RP_3$ and a projection lens $L_3$. The projection lens $L_3$ is disposed so as to oppose the lens $E_1$ of the eye E to be examined. The pentagonal prism $RP_1$ is adapted to reflect vertically downwardly the light coming from the light source F through the lenses $L_1$ and $L_2$. The light is then reflected forwardly by the prism $RP_2$ toward the projection lens $L_3$.

Interposed between the lenses $L_1$ and $L_2$ is a target T which is movable in the direction of the optical axis. The target T is composed of two semi-circular target plates $D_1$, $D_2$. The target plate $D_1$ is provided with a target element $T_1$ for measuring the refractive power and a target element $T_2$ for detecting the astigmatic axis, while the target plate $D_2$ is provided with a target element $T_3$ for measuring the refractive power and a target element $T_4$ for detecting the astigmatic axis.

The target element $T_1$ comprises a pair of parallel slits $S_1$, $S_2$, and pairs of deflection prisms $P_1$, $P_2$, $P_3$, $P_4$ combined with respective ones of the slits $S_1$, $S_2$. The prisms $P_1$, $P_2$ associated with the slit $S_1$ have oppositely directed deflection angles. Similarly, prisms $P_3$, $P_4$ associated with the slit $S_2$ have oppositely directed deflection angles. The target element $T_3$ has a pair of slits $S_3$, $S_4$ which are arranged at right angles to the slits $S_1$, $S_2$. Pairs of deflection prisms $P_5$, $P_6$, $P_7$, $P_8$ are combined with respective ones of these slits $S_3$, $S_4$ in the same manner as in the target element $T_1$.

The target element $T_2$ has a pair of parallel slits $S_5$, $S_6$ arranged at right angles to the slits $S_1$, $S_2$. These slits $S_5$, $S_6$ are combined with respective pairs of prisms $P_9$, $P_{10}$, $P_{11}$, $P_{12}$. These prisms have deflection angles directed longitudinally of the slits. The prisms $P_9$ and $P_{10}$ associated with the slit $S_5$ have oppositely directed deflection angles. Similarly, the prisms $P_{11}$, $P_{12}$ associated with the slit $S_6$ have oppositely directed deflection angles. The target element $T_4$ has a pair of slits $S_7$, $S_8$ arranged to right angle to the slits $S_5$, $S_6$. These slits $S_7$, $S_8$ are combined with respective pairs of deflection prisms $P_{13}$, $P_{14}$, $P_{15}$, $P_{16}$ in the same manner as in the target element $T_2$. Four apertures $A_1$, $A_2$, $A_3$, $A_4$ corresponding to the four target elements $T_1$, $T_2$, $T_3$, $T_4$ of the target are disposed between the prism $RP_1$ and the prism $RP_2$ having the bore, so that the image of the filament of the light source F is focussed at the points of these apertures $A_1$, $A_2$, $A_3$, $A_4$ through the lens $L_1$, target T, lens $L_2$ and the prism $RP_1$. The eye E to be examined is so located that the lens $E_1$ of the eye is conjugate with the apertures $A_1$, $A_2$, $A_3$, $A_4$ with respect to the projection lens $L_3$.

The observation optical system comprises lenses $L_4$, $L_5$ by means of which the slit image focussed on the fundus is observed through the lens $L_3$ and the bore of the prism $RP_2$.

FIG. 2 shows a target image formed on the fundus of the eye when the target $T_2$ for detection of the astigmatic axis is placed in the projected light path. More specifically, FIG. 2a shows the state in which the direction of the target image is not in coincidence with the astigmatic axis. As the image rotator $RP_3$ is operated in this state to bring the direction of the target image into coincidence with one of the astigmatic axes, the slit images $S_5'$-$S_8'$ of the target elements $T_2$, $T_4$ are aligned in a linear manner as shown in FIG. 2b provided that the astigmatism of the examined eye E is regular astigmatism. If this is not the case, one of the groups of slit images, e.g. slit images $S_5'$, $S_6'$ remain out of alignment, as shown in FIG. 2a. Thus, the state of the irregular astigmatism is easily detected simultaneously with the detection of the astigmatic axis. Needless to say, the same effect is obtained also by rotating the whole optical system.

Figure 2C:
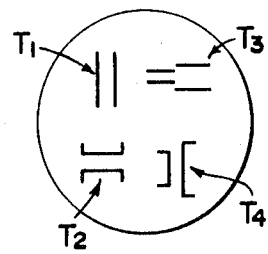
Figure 2D:
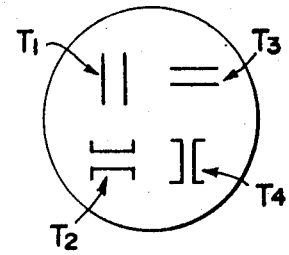

As the target plates $D_1$ and $D_2$ are moved simultaneously in the direction of the optical axis, the projection image of one of the target elements $T_1$, $T_3$, e.g. the target element $T_1$, assumes the focussed state as shown in FIG. 2c. As only the target plate $D_2$ is moved in this state independently in the direction of the optical axis, the projection image of the target image $T_3$ is also focussed, as shown in FIG. 2d. The refractive power and the degree of astigmia are known from the positions of the target plates $D_1$ and $D_2$. Also, the orientations of the astigmatic axes are known from the rotation angle of the image rotator $RP_3$.

FIGS. 3 and 4 show an example of the target supporting mechanism. The target plates $D_1$, $D_2$ are attached to respective support brackets 1, 2. The support bracket 1 is fixed to a reciprocating carriage 3, while the support bracket 2 is fixed to a sliding base 4 adapted to slide in a slot 3a of the reciprocating carriage 3. A rack 5 attached to one side of the reciprocating carriage 3 meshes with a pinion 8 fixed to an operation shaft 7 of an operation knob 6. A manipulation knob 9 is mounted coaxially with the manipulation knob 6. A drum member 10 having a cylindrical pulley surface 10a is slidably attached to the operation knob 9 for axial movement.

A potentiometer 11 has two shafts 11a, 11b extending from both sides thereof. A pulley 12 is attached to one 11a of these shafts. A belt 13 is stretched between the pulley surface 10a and the pulley 12. A gear 14 attached to the other 11b of the shafts of the potentiometer 11 meshes with a rack 4a formed in the lower side of the sliding bed 4. The operation knobs 6 and 9 are disposed to make frictional contact at their cylindrical surfaces 6a, 9a. The operation knob 9 is urged toward the operation knob 6 by a spring 15. Therefore, the operation knob 9 is rotated together with the operation knob 6 as the latter is rotated, so that the brackets 1, 2 are moved simultaneously in the same direction. Then, as the operation knob 9 is depressed in the direction of the arrow and rotated, the bracket 2 alone is moved independently of the bracket 1.

The invention has thus been shown and described with reference to a specific embodiment, however, it should be noted that the invention is in no way limited to the details of the illustrated structures but changes and modifications may be made without departing from the scope of the appended claims.

We claim:

1. A refractory power measuring device comprising a target projecting optical system for optically projecting a target through an optical body to be inspected to produce an image of the target, said target projecting optical system including means for moving the target along an optical axis of the system, means for observing the image of the target to locate a position of the target along the optical axis wherein the image of the target is focussed at a predetermined position, said target including two optical elements adapted for measuring refractory powers in orientations perpendicular with each other, one of said optical elements being at one side of the optical axis and the other being at the other side of the optical axis, said two optical elements being located close to each other and movable generally parallel to the optical axis independently from and without any interference with each other.

2. A refractory power measuring device in accordance with claim 1 in which one of the optical elements comprises a pair of slits oriented in one direction and deflecting prisms respectively associated with the slits for deflecting light beams through the slits in a direction perpendicular to the slits, the direction of deflection of one prism being opposite to that of the other prism, the other optical element comprising at least a pair of slits which are perpendicular to the first pair of slits and respectively associated with deflecting prisms.

3. A refractory power measuring device in accordance with claim 1 in which at least one of the optical elements is provided with means for detecting an astigmatic axis.

4. A refractory power measuring device in accordance with claim 3 in which said means for detecting astigmatic axis include a pair of slits oriented in one direction and deflecting prisms which are respectively associated with the slits with directions of deflection opposite to each other and along longitudinal axes of the slits.

5. A refractory power measuring device in accordance with claim 1 in which the target moving means includes a first mechanism for moving the optical elements as a unit and a second mechanism for moving the optical elements independently.

* * * * *